United States Patent [19]

Giusti et al.

[11] Patent Number: 5,003,125
[45] Date of Patent: Mar. 26, 1991

[54] PROCESS FOR OLIGOMERIZING LIGHT OLEFINS

[75] Inventors: Aldo Giusti, Lucca; Stefano Gusi, Bologna; Giuseppe Bellussi, Piacenza; Vittorio Fattore, San Donato Milanese, all of Italy

[73] Assignees: Eniricerche S.p.A.; AGIP S.p.A., both of Milan, Italy

[21] Appl. No.: 372,091

[22] Filed: Jun. 28, 1989

Related U.S. Application Data

[63] Continuation of Ser. No. 135,438, Dec. 21, 1987, abandoned.

[30] Foreign Application Priority Data

Dec. 23, 1986 [IT] Italy .................... 22812 A/86

[51] Int. Cl.$^5$ .................................... C07C 2/10
[52] U.S. Cl. .................. 585/530; 423/326; 585/415; 585/417; 585/531
[58] Field of Search ............... 423/326; 585/415, 417, 585/530, 531

[56] References Cited

U.S. PATENT DOCUMENTS

| | | | |
|---|---|---|---|
| 4,831,201 | 5/1989 | Giusti et al. | 585/530 |
| 4,831,202 | 5/1989 | Giusti et al. | 585/530 |

*Primary Examiner*—Asok Pal
*Attorney, Agent, or Firm*—Birch, Stewart, Kolasch & Birch

[57] ABSTRACT

The present invention relates to a process for the oligomerization of light olefins or mixtures thereof, wherein a reaction is brought about between olefins with a carbon number of between 2 and 20 and synthetic zeolites containing silicon, titanium and gallium oxides which in the calcined, anyhdrous state have the following empirical formula:

$$pHGaO_2 \cdot qTiO_2 \cdot SiO_2,$$

where p is of a value greater than zero and less than or equal to 0.050 and q is of value greater than zero and less than or equal to 0.025, with the H$^+$ of HGaO$_2$ being at least partly exchangeable or exchanged with cations.

13 Claims, 1 Drawing Sheet

PROCESS FOR OLIGOMERIZING LIGHT OLEFINS

This application is a continuation of application Ser. No. 07/135,438 filed on Dec. 21, 1987, now abandoned.

BACKGROUND OF THE INVENTION

1. Field of the Invention

The present invention concerns a process for oligomerizing light olefines using a particular synthetic porous crystalline substance.

2. Discussion of Prior Art

A number of processes are known for the oligomerization of olefins using synthetic zeolites as catalysts. There are well-known processes, the subject of U.S. Pat. Nos. 3,756,942, 3,760,024, 3,775,501, 3,827,968, 3,960,978, 4,021,502, 4,150,062 and 4,227,992, for the production of benzenes of a high octane number from olefins with the use of zeolites of the "ZSM" type, i.e., zeolites consisting of silicon and aluminum oxides.

Another method that is known, described in the published "Proceedings of the VIII International Congress on Catalysis" (Berlin 1984, p. 569), is the use for such processes of a zeolite consisting of silicon and gallium oxides.

SUMMARY OF THE INVENTION

We have discovered that a synthetic zeolite containing silicon, titanium and gallium oxides can oligomerize light olefines with a higher degree of selectivity and conversion, at the equivalent temperature, than can be obtained with the use of the catalysts previously mentioned, whilst at the same time its catalytic properties are preserved for considerably longer periods.

DETAILED DESCRIPTION OF THE INVENTION

Figure 1:
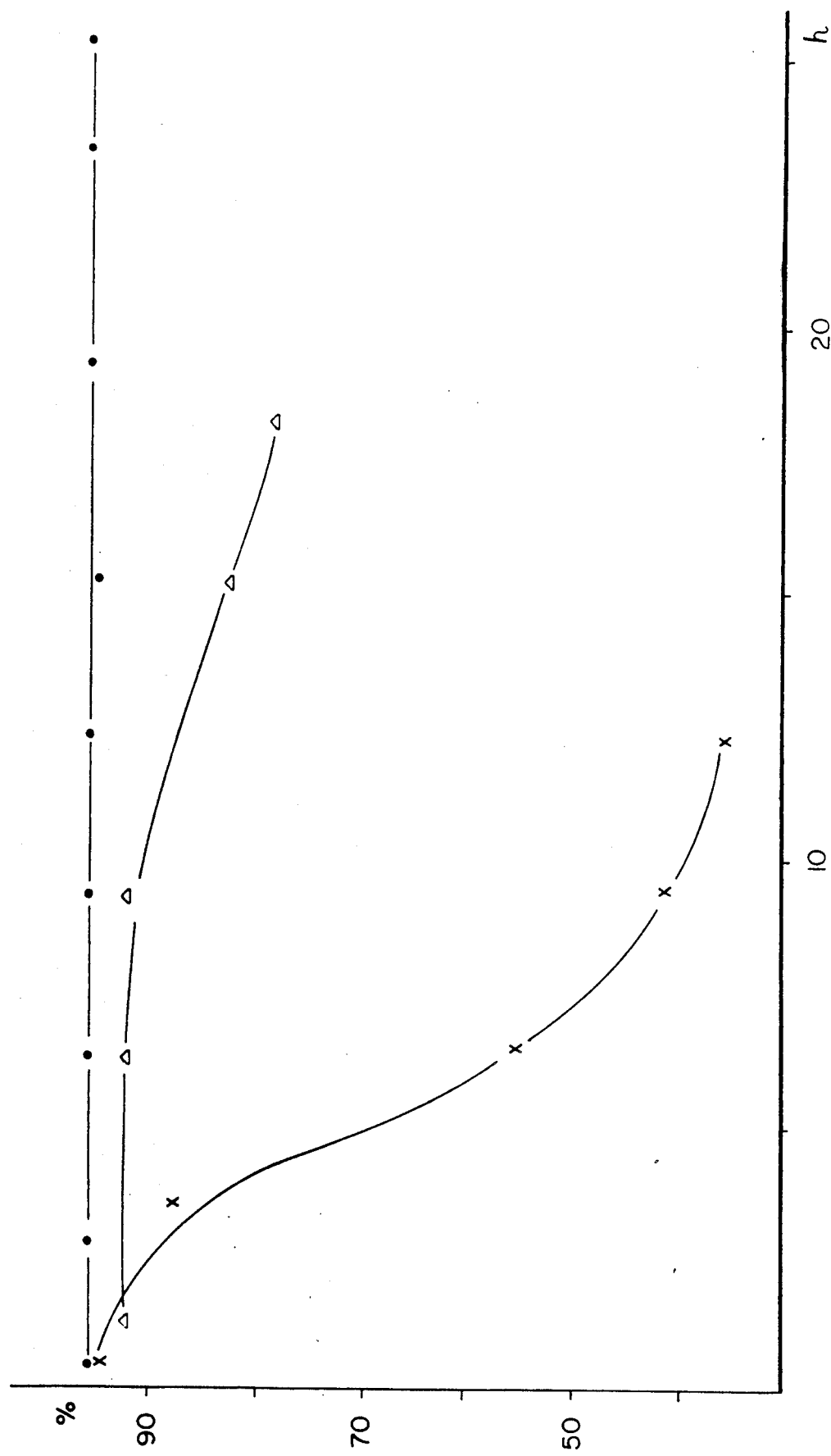
FIG. 1 shows the conversions in percent as a function of processing running time.

The subject of the present invention is a process for oligomerizing light olefins and mixtures thereof whereby such olefins, where appropriately diluted by means of an inert gas, are caused to react with synthetic zeolites containing silicon, titanium and gallium oxides which in the calcined, anhydrous state have the following empirical formula:

$$pHGaO_2 \cdot qTiO_2 \cdot SiO_2,$$

where p is of a value greater than zero and less than or equal to 0.050 and q of a value greater than zero and less than or equal to 0.025, with the $H^+$ of $HGaO_2$ being at least partly exchangeable or exchanged with cations.

The transition from a cationic to a different form can be effected by the customary procedures for exchange of a kind that is well-known.

The oligomerization reaction is carried out at a temperature of between 220 and 300 degrees Celsius, preferably between 230 and 270 degrees Celsius, at a pressure of preferably between 1 and 30 atm and a spatial velocity—WHSV (weight hourly space velocity)—of between 0.1 and 10 $h^{-1}$, preferably between 0.3 and 5 $h^{-1}$.

The number of carbon atoms in the light olefines is between 2 and 20, usually between 2 and 4.

The products obtained from this process are predominantly olefins and aromatic hydrocarbons with carbon atoms numbering between 5 and 20.

Synthetic zeolites containing silicon, titanium and gallium oxides as described above are seen to be crystalline when X-rayed.

They have been analysed by means of a diffractometer for powder samples, equipped with an electronic pulse-counting system utilizing CuK$\alpha$ radiation. For calculating strength values the peak levels were measured and expressed as percentages in relation to the strongest peak.

The principal reflections from analysis of the calcined, anhydrous product are characterized by the values given in Table 1 under d (d = the interplanar distance):

TABLE 1

| d (Å) | Relative Strength |
|---|---|
| 11.14 ± 0.10 | vs |
| 9.99 ± 0.10 | s |
| 9.74 ± 0.10 | m |
| 6.36 ± 0.07 | mw |
| 5.99 ± 0.07 | mw |
| 4.26 ± 0.05 | mw |
| 3.86 ± 0.04 | s |
| 3.82 ± 0.04 | s |
| 3.75 ± 0.04 | s |
| 3.72 ± 0.04 | s |
| 3.65 ± 0.04 | m |
| 3.05 ± 0.02 | mw |
| 2.99 ± 0.02 | mw |

(where vs = very strong, s = strong, m = medium, mw = medium weak).

The zeolites we have used have an IR spectrum with the following more significant wn values (wn = the wave number):

| wn(cm$^{-1}$) | Relative Strength |
|---|---|
| 1220–1230 | w |
| 1080–1110 | s |
| 965–975 | mw |
| 795–805 | mw |
| 550–560 | m |
| 450–470 | ms | s = strong, ms = medium strong, m = medium, mw = medium weak, w = weak.

The preparation process for obtaining the zeolites described is characterized by a reaction brought about in hydrothermal conditions between a derivative of silicon, a derivative of titanium, a derivative of gallium and a nitrogenous organic base, with a $SiO_2/Ga_2O_3$ reagents' molar ratio greater than 100, and preferably between 150 and 600, a $SiO_2/TiO_2$ reagents' molar ratio of greater than 5, and preferably between 15 and 25, and a $H_2O/SiO_2$ reagents' molar ratio of preferably between 30 and 50, in the presence as appropriate of a salt or salts and/or alkaline hydroxides or alkaline earths with a M/SiO$_2$ (where M is the alkaline cation and/or alkaline earth) reagents' molar ratio less than 0.1, and preferably less than 0.01 or zero.

In the empirical formula for the substance, gallium has been expressed in the form $HGaO_2$ to indicate that it is in $H^+$ form.

When mentioning the ratios between the different reagents we use the symbol $Ga_2O_3$ for gallium, since this is the more usual form.

The silicon derivative is selected from among silica gel, silica sol and alkyl silicates, preferably tetraethylsilicate; the titanium derivative is selected from among salts such as the halides and among organic derivatives of titanium such as the alkyl titanates, preferably tetraethyltitanate; the gallium derivative is selected from among salts such as the halides or the nitrates or the hydroxides.

The nitrogenous organic base can be an alkyl ammonium hydroxide, preferably tetrapropylammonium hydroxide.

If tetrapropylammonium hydroxide is used, the TPA+/$SiO_2$ (where TPA=tetrapropylammonium) reagents' ratio is between 0.2 and 1.0, preferably between 0.2 and 0.4. The reagents are induced to react at a temperature of between 100 and 200 degrees Celsius, at a pH of between 9 and 14, preferably between 10 and 12, and for a period of time varying between 1 hour and 5 days.

The titanium-gallium-silicalite is recovered by filtration and centrifuging, washed, dried, calcined at a temperature of preferably between 500 and 600 degrees Celsius for a period of, preferably, between 4 and 8 hours, and then exchanged in acid form in accordance with the known procedures of the art.

Under a different form of procedure, the titanium-gallium-silicalite can be bonded with amorphous oligomeric silica, with a molar ratio between oligomeric silica and titanium-gallium-silicalite of between 0.05 and 0.12, whereby the crystals of titanium-gallium-silicalite are caged by Si—O—Si bridges, the mass of titanium-gallium-silicalite crystals with silica being in the form of microspheres 5–1000 μm in diameter.

With another method again, the matter obtained, either as such or in the form of microspheres, can be pelletized or extruded to obtain pellets or extrusions of the desired dimensions and then calcined up to a temperature of between, preferably, 500 and 600 degrees Celsius.

A support can also be added to the titanium-gallium-silicalite, as such or bonded, in the form of one of the more or less inert substances that are well-known from the literature of the art, such as aluminas, kaolins, silicas, etc., varying in relative quantity, weight, between 10 and 40%, preferably between 15 and 35%. The mixture is then moulded and calcined.

The olefins used for the oligomerization reaction, with a composition of between $C_2$ and $C_{10}$, can be ethylene, propylene, 1-butene, 2-butene cis and trans, isobutene, etc. They can be used on their own or in combinations.

They can also be used undiluted or diluted with inert substances such as nitrogen, methane, ethane, butane and other higher paraffins, etc., as well as with a part of the reaction products.

Any olefins failing to react can be separated out by traditional methods and recycled.

The oligomerization reaction can be conducted in a fixed or fluidized bed; reaction temperatures and pressures and reagent flows can vary widely, dependent on the particular nature of the mixture with which the reactor is charged.

We give some examples below to illustrate the significance of the present invention. They should not be taken to be exhaustive with regard to the scope of the invention.

EXAMPLE 1

6.1 g of $Ga(NO_3)_3 \cdot 8H_2O$ are dissolved in 70 g of $C_2H_5OH$ and the solution obtained is added under mild agitation to a solution comprising 22.7 g of tetraethyltitanate and 416 g of tetraethylsilicate.

The clear, alcoholic solution thus obtained is added under moderate agitation to 870 g of an aqueous solution of 14% tetrapropylammonium hydroxide. The mixture is kept under constant agitation, and is heated as appropriate till a clear single-phase liquid is obtained. 700 g of demineralized water are next added, and agitation is continued for a further hour. The resulting mixture is then placed in a stainless steel autoclave, agitated, and heated under autogenous pressure to a temperature of 170 degrees Celsius. These conditions are maintained for 15 hours, after which the autoclave is cooled and discharged. The resulting suspension is centrifuged and the solid matter washed, by redispersal and centrifuging, dried at 120 degrees Celsius and finally calcined at 550 degrees Celsius for 4 hours.

The product thus obtained is then exchanged by the well-known procedures in proton form.

Chemical analysis gives the following composition for the anhydrous product: $SiO_2/Ga_2O_3 = 195$ and $SiO_2/TiO_2 = 54$. Powder analysis by X-ray diffraction demonstrates that the product is crystalline.

The product is pelletized by pressing and subsequently granulated in sizes between 10 and 40 ASTM mesh.

EXAMPLES 2–3

The methods described at Example 1 are used for two other preparations: Table 1 gives the molar compositions of the reagent mixtures and the resulting products, obtained by chemical analysis.

In Example 2, crystallization was effected at 170° C. for 15 hours, and in Example 3 at 100° C. over 5 days.

TABLE 1

| Ex. Moles | Composition of Reaction Mixture | | | | Composition of Products | |
|---|---|---|---|---|---|---|
| | $SiO_2/TiO_2$ | $SiO_2Ga_2/O_3$ | TPA*/$SiO_2$ | $H_2O/SiO_2$ | $SiO_2/TiO_2$ | $SiO_2/Ca_2O_3$ |
| 1 | 20 | 250 | 0.3 | 40 | 54 | 195 |
| 2 | 50 | 450 | 0.3 | 40 | 54 | 414 |
| 3 | 20 | 600 | 0.3 | 40 | 43 | 641 |

EXAMPLE 4

A steel reactor with an inside diameter of 8 mm, heated by an electric fire, is charged with 1.5 cc of titanium-gallium-silicalite prepared as in Example 1 ($SiO_2/Ga_2O_3 = 195$; $SiO_2/TiO_2 = 54$).

The catalyst is heated in nitrogen up to the reaction temperature, when propylene is added.

The process conditions and the results obtained are as follows:

| | |
|---|---|
| Temperature | 240° C. |
| Pressure | 1 atm |
| WHSV | 0.6 h$^{-1}$ |
| $C_3H_6/N_2$ ratio | ½ (volume for volume) |
| $C_3H_6$ conversion | 45% (weight for weight) |
| Yield in $C_5$ and higher carbon atom nos. | 37% (weight for weight) |
| Selectivity in | % (weight for weight) |

| | |
|---|---|
| -continued | |
| $C_2$ | 0.2 |
| $C_3H_8$ | traces |
| $C_4$ | 19 |
| $C_5$ | 21 |
| $C_6$ | 22 |
| $C_7$ and higher carbon atom nos. | 38 |

For this and the subsequent examples, WHSV (weight hourly space velocity) is defined as:

$$\frac{\text{weight of olefine used}}{\text{weight of catalyst}} \times \frac{1}{h}$$

EXAMPLE 5

The same type of reactor as in Example 4 is charged with 1.5 cc of titanium-gallium-silicalite prepared as in Ex. 1 ($SiO_2/Ga_2O_3=195$; $SiO_2/TiO_2=54$).

The catalyst is heated in nitrogen to reaction temperature and then propylene is added.

The process conditions and the results obtained are as follows:

| | |
|---|---|
| Temperature | 260° C. |
| Pressure | 1 atm |
| WHSV | 0.6 h$^{-1}$ |
| $C_3H_6/N_2$ | ½ (volume for volume) |
| $C_3H_6$ conversion | 96% (weight for weight) |
| Yield in $C_5$ and higher carbon atom nos. | 77% (weight for weight) |
| Selectivity in | % (weight for weight) |
| $C_2$ | 0.3 |
| $C_3H_8$ | traces |
| $C_4$ | 19 |
| $C_5$ | 23 |
| $C_6$ | 18 |
| $C_7$ and higher carbon atom nos. | 39 |

EXAMPLE 6

A reactor of the same type as in Example 4 is charged with 1.5 cc of titanium-gallium-silicalite prepared as in Example 1 ($SiO_2/Ga_2O_3=195$; $SiO_2/TiO_2=54$).

The catalyst is heated to reaction temperature in nitrogen and then 1-butene is added.

The process conditions and results obtained are as follows:

| | |
|---|---|
| Temperature | 260° C. |
| Pressure | 1 atm |
| WHSV | 0.6 h$^{-1}$ |
| 1-$C_4H_8$ ratio | ½ (volume for volume) |
| 1-$C_4H_8$ conversion | 91% (weight for weight) |
| Yield in $C_5$ and higher carbon atom nos. | 77% (weight for weight) |
| Selectivity in | % (weight for weight) |
| $C_2$ | 0.2 |
| $C_3$ | 4 |
| $C_4$ | 11 |
| $C_5$ | 29 |
| $C_6$ | 24 |
| $C_7$ and higher carbon atom nos. | 32 |

EXAMPLE 7

A reactor of the same type as in Example 4 is charged with 1.5 cc of titanium-gallium-silicalite prepared as in Ex. 2 ($SiO_2/Ga_2O_3=414$; $SiO_2/TiO_2=54$).

The catalyst is heated in nitrogen to reaction temperature and then propylene is added.

The process conditions and results obtained are as follows:

| | |
|---|---|
| Temperature | 240° C. |
| Pressure | 1 atm |
| WHSV | 0.6 h$^{-1}$ |
| $C_3H_6/N_2$ ratio | ½ (volume for volume) |
| $C_3H_6$ conversion | 69% (weight for weight) |
| Yield in $C_5$ and higher carbon atom nos. | 56% (weight for weight) |
| Selectivity in | (weight for weight) |
| $C_2$ | 0.2 |
| $C_3H_8$ | traces |
| $C_4$ | 18 |
| $C_5$ | 20 |
| $C_6$ | 20 |
| $C_7$ and higher carbon atom nos. | 42 |

EXAMPLE 8

A reactor of the same type as in Example 4 is charged with 1.5 cc of titanium-gallium-silicalite prepared as in Ex. 2 ($SiO_2/Ga_2O_3=414$; $SiO_2/TiO_2=54$).

The catalyst is heated to reaction temperature in nitrogen and then propylene is added.

The process conditions and results obtained are as follows:

| | |
|---|---|
| Temperature | 260° C. |
| Pressure | 1 atm |
| WHSV | 0.6 h$^{-1}$ |
| $C_3H_6/N_2$ ratio | ½ (volume for volume) |
| $C_3H_6$ conversion | 96% (weight for weight) |
| Yield in $C_5$ and higher C atom nos. | 79% (weight for weight) |
| Selectivity in | % (weight for weight) |
| $C_2$ | 0.3 |
| $C_3H_8$ | traces |
| $C_4$ | 17 |
| $C_5$ | 23 |
| $C_6$ | 19 |
| $C_7$ and higher C atom nos. | 41 |

EXAMPLE 9

A reactor of the same type as in Example 4 is charged with 1.5 cc of titanium-gallium-silicalite prepared as in Ex. 3 ($SiO_2/Ga_2O_3=641$; $SiO_2/TiO_2=43$).

The catalyst is heated in nitrogen to reaction temperature and then propylene is added.

The process conditions and results obtained are as follows:

| | |
|---|---|
| Temperature | 240° C. |
| Pressure | 1 atm |
| WHSV | 0.6 h$^{-1}$ |
| $C_3H_6/N_2$ ratio | ½ (volume for volume) |
| $C_3H_6$ conversion | 84% (weight for weight) |
| Yield in $C_5$ and higher C atom nos. | 69% (weight for weight) |
| Selectivity in | % (weight for weight) |
| $C_2$ | 0.1 |
| $C_3H_8$ | traces |
| $C_4$ | 18 |
| $C_5$ | 22 |
| $C_6$ | 21 |
| $C_7$ and higher C atom nos. | 39 |

EXAMPLE 10

A reactor of the same type as in Example 4 is charged with 1.5 cc of titanium-gallium- silicalite prepared as in Ex. 3 ($SiO_2/Ga_2O_3=641$; $SiO_2/TiO_2=43$).

The catalyst is heated in nitrogen to reaction temperature and then propylene is added.

The process conditions and results obtained are as follows:

| | |
|---|---|
| Temperature | 260° C. |
| Pressure | 1 atm |
| WHSV | 0.6 h$^{-1}$ |
| $C_3H_6/N_2$ ratio | ⅛ (volume for volume) |
| $C_3H_6$ conversion | 97% (weight for weight) |
| Yield in $C_5$ and higher C atom nos. | 82% (weight for weight) |
| Selectivity in | % (weight for weight) |
| $C_2$ | 0.2 |
| $C_3H_8$ | traces |
| $C_4$ | 15 |
| $C_5$ | 20 |
| $C_6$ | 15 |
| $C_7$ and higher C atom nos. | 49 |

EXAMPLE 11

A reactor of the same type as in Example 4 is charged with 1.5 cc of titanium-gallium-silicalite prepared as in Ex. 3 ($SiO_2/Ga_2O_3=641$; $SiO_2/TiO_2=43$).

The catalyst is heated to reaction temperature in nitrogen and 1-butene is added.

The process conditions and results obtained are as follows:

| | |
|---|---|
| Temperture | 260° C. |
| Pressure | 1 atm |
| WHSV | 0.6 h$^{-1}$ |
| 1-$C_4H_8/N_2$ ratio | ⅛ (volume for volume) |
| 1-$C_4H_8$ conversion | 91% (weight for weight) |
| Yield in $C_5$ and higher carbon atom nos. | 78% (weight for weight) |
| Selectivity in | % (weight for weight) |
| $C_2$ | 0.2 |
| $C_3$ | 4 |
| $C_4$ | 10 |
| $C_5$ | 27 |
| $C_6$ | 22 |
| $C_7$ and higher carbon atom nos. | 38 |

EXAMPLE 12 (COMPARATIVE)

A reactor of the same type as in Example 4 is charged with 1.5 cc of a zeolite comprised of silicon and gallium oxides with a $SiO_2/Ga_2O_3$ ratio of 250.

The catalyst is heated in nitrogen to reaction temperature and then propylene is added.

The process conditions and results obtained are as follows:

| | |
|---|---|
| Temperature | 240° C. |
| Pressure | 1 atm |
| WHSV | 0.6 h$^{-1}$ |
| 1-$C_3H_6/N_2$ ratio | ⅛ (volume for volume) |
| 1-$C_3H_6$ conversion | 23% (weight for weight) |
| Yield in $C_5$ and higher C atom nos. | 18% (weight for weight) |
| Selectivity in | % (weight for weight) |
| $C_2$ | 0.2 |
| $C_3H_8$ | traces |
| $C_4$ | 21 |
| $C_5$ | 22 |
| $C_6$ | 26 |
| $C_7$ and higher C atom nos. | 31 |

It is pointed out that in this case the conversion levels and the yield in $C_5$ and higher carbon atom numbers are lower than those found with Examples 4 and 7.

EXAMPLE 13 (COMPARATIVE)

A reactor of the same type as in Example 4 is charged with 1.5 cc of a zeolite comprised of silicon and gallium oxides with a $SiO_2/Ga_2O_3$ ratio of 250.

The catalyst is heated to reaction temperature and then propylene is added.

The process conditions and results obtained are as follows:

| | |
|---|---|
| Temperature | 260° C. |
| Pressure | 1 atm |
| WHSV | 0.6 h$^{-1}$ |
| $C_3H_6/N_2$ ratio | ⅛ (volume for volume) |
| $C_3H_6$ conversion | 96% (weight for weight) |
| Yield in $C_5$ and higher C atom nos. | 78% (weight for weight) |
| Selectivity in | % (weight for weight) |
| $C_2$ | 0.2 |
| $C_3H_8$ | traces |
| $C_4$ | 18 |
| $C_5$ | 24 |
| $C_6$ | 20 |
| $C_7$ and higher C atom nos. | 38 |

Although conversion levels and yield in $C_5$ and higher carbon atom numbers are the same as in Example 5, stability diminishes with time, as illustrated at FIG. 1.

EXAMPLE 14

A reactor of the same type as in Example 4 is charged with 1.5 cc of a zeolite comprised of silicon and gallium oxides with a $SiO_2/Ga_2O_3$ ratio of 565.

The catalyst is heated to reaction temperature and then propylene is added.

The process conditions and results obtained are as follows:

| | |
|---|---|
| Temperature | 240° C. |
| Pressure | 1 atm |
| WHSV | 6 h$^{-1}$ |
| $C_3H_6/N_2$ ratio | ⅛ (volume for volume) |
| $C_3H_6$ conversion | 30% (weight for weight) |
| Yield in $C_5$ and higher C atom nos. | 24% (weight for weight) |
| $C_2$ | 0.3 |
| $C_3H_8$ | traces |
| $C_4$ | 19 |
| $C_5$ | 21 |
| $C_6$ | 24 |
| $C_7$ and higher C atom nos. | 36 |

It is pointed out that in this case the conversion levels and the yield in $C_5$ and higher carbon atom numbers are lower than those found with Examples 7 and 9.

EXAMPLE 15 (COMPARATIVE)

A reactor of the same type as in Example 4 is charged with 1.5 cc of a zeolite comprised of silicon and gallium oxides with a $SiO_2/Ga_2O_3$ ratio of 250.

The catalyst is heated to reaction temperature and then 1-butene is added.

The process conditions and results obtained are as follows:

| | |
|---|---|
| Temperature | 260° C. |
| Pressure | 1 atm |
| WHSV | 0.6 h$^{-1}$ |
| 1-$C_4H_8/N_2$ ratio | ⅛ (volume for volume) |
| 1-$C_4H_8$ conversion | 91% (weight for weight) |
| Yield in $C_5$ and higher C atom nos. | 74% (weight for weight) |
| Selectivity in | % (weight for weight) |
| $C_2$ | 0.2 |

| -continued | |
|---|---|
| $C_3H_8$ | 5 |
| $C_4$ | 14 |
| $C_5$ | 23 |
| $C_6$ | 20 |
| $C_7$ and higher C atom nos. | 38 |

It is pointed out that in this case the yield levels in $C_5$ and higher carbon atom numbers are lower than those found in Examples 6 and 11.

EXAMPLE 16 (COMPARATIVE)

A reactor of the same type as in Example 4 is charged with 1.5 cc of a ZSM-5 zeolite with a $SiO_2/Al_2O_3$ ratio of 35.

The catalyst is heated to reaction temperature and then propylene is added.

The process conditions and results obtained are as follows:

| Temperature | 260° C. |
|---|---|
| Pressure | 1 atm |
| WHSV | 0.6 h$^{-1}$ |
| $C_3H_6/N_2$ ratio | 1/4 (volume for volume) |
| $C_3H_6$ conversion | 63% (weight for weight) |
| Yield in $C_5$ and higher C atom nos. | 48% (weight for weight) |
| Selectivity in | % (weight for weight) |
| $C_2$ | 0.2 |
| $C_3H_8$ | 0.3 |
| $C_4$ | 23 |
| $C_5$ | 23 |
| $C_6$ | 20 |
| $C_7$ and higher C atom nos. | 33 |

It is pointed out that in this case the yield levels in $C_5$ and higher carbon atom numbers are lower than those found in Examples 5, 8 and 10.

EXAMPLE 17 (COMPARATIVE)

A reactor of the same type as in Example 4 is charged with 1.5 cc of a ZSM-5 zeolite with a $SiO_2/Al_2O_3$ ratio of 35.

The catalyst is heated to reaction temperature and then propylene is added.

The process conditions and results obtained are as follows:

| Temperature | 300° C. |
|---|---|
| Pressure | 1 atm |
| WHSV | 0.6 h$^{-1}$ |
| $C_3H_6/N_2$ ratio | 1/4 (volume for volume) |
| $C_3H_6$ conversion | 92% (weight for weight) |
| Yield in $C_5$ and higher C atom nos. | 67% (weight for weight) |
| Selectivity in | % (weight for weight) |
| $C_2$ | 0.4 |
| $C_3H_8$ | 1 |
| $C_4$ | 26 |
| $C_5$ | 28 |
| $C_6$ | 19 |
| $C_7$ and higher C atom nos. | 26 |

FIG. 1 gives the conversions in % (weight for weight) as a function of the process running time. The dots are in reference to Example 5, the crosses to the comparative Example 13 and the triangles to the comparative Example 17.

As can be seen, the catalyst we use is more stable than the ones used previously.

We claim:

1. A process for oligomerizing light olefins and mixtures thereof, which comprises reacting olefins having a carbon number of between 2 and 20 with synthetic zeolites having the X-ray diffraction pattern set forth in Table 1 and comprising silicon, titanium and gallium oxides bonded together in an integrated crystalline structure and which in the calcined, anhydrous state have the following empirical formula:

$$pHGaO_2 \cdot qTiO_2 \cdot SiO_2,$$

wherein p is of a value greater than zero and less than or equal to 0.050 and q is of a value greater than zero and less than or equal to 0.025, with the H+ of $HGaO_2$ being at least partly exchangeable or exchanged with cations, and wherein the reaction process is carried out at a temperature of between 220 and 300 degrees Celsius and at a weight hourly space velocity of between 0.1 and 10 h$^{-1}$.

2. The process of claim 1, wherein the reaction is conducted at a temperature of between 230 and 270 degrees Celsius.

3. The process of claim 1, wherein the reaction is carried out at a weight hourly space velocity of between 0.3 and 5 h$^{-1}$.

4. The process of claim 1, wherein the reaction is conducted at a pressure of between 1 and 30 atm.

5. The process of claim 1, wherein the olefins have a carbon atom count of between 2 and 4.

6. The process of claim 1, wherein the synthetic zeolites are bonded having amorphous oligomeric silicon with a molar ratio between amorphous silicon and zeolites of between 0.05 and 0.12, the zeolite crystals being mutually caged by Si—O—Si bridges and the mass of zeolite crystals with silicon being in the form of microspheres of between 5 and 1000 μm in diameter.

7. The process of claim 1, wherein a support is added to the synthetic zeolites comprising an inert substance.

8. The process of claim 1, wherein the olefins are diluted with an inert gas.

9. The process of claim 1, wherein 10 to 40% of the support comprises at least one of an inert substance of alumina, kaolin or silica.

10. The process of claim 1, wherein the olefins have a carbon number of between 2 and 10.

11. The process of claim 1, wherein the olefins are selected from the group consisting of ethylene, propylene, 1-butene, cis and trans 2-butene, isobutene and mixtures thereof.

12. The process of claim 8, wherein the inert substance is selected from the group consisting of nitrogen, methane, ethane and butane.

13. A process for oligomerizing light olefins and mixtures thereof, which comprises reacting olefins having a carbon number of between 2 and 20 with synthetic zeolites having the X-ray diffraction pattern set forth in Table 1 and consisting essentially of silicon, titanium and gallium oxides bonded together in an integrated crystalline structure and which in the calcined, anhydrous state have the following empirical formula:

$$pHGaO_2 \cdot qTiO_2 \cdot SiO_2,$$

wherein p is of a value greater than zero and less than or equal to 0.050 and q is of a value greater than zero and less than or equal to 0.025, with the H+ of $HGaO_2$ being at least partly exchangeable or exchanged with cations, and wherein the reaction process is carried out at a temperature of between 220° and 300° C. and at a weight hourly space velocity of between 0.1 and 10 h$^{-1}$.

* * * * *